United States Patent [19]

Maier et al.

[11] Patent Number: 5,780,443
[45] Date of Patent: Jul. 14, 1998

[54] WATER-SOLUBLE RETINOIDS

[75] Inventors: Thomas Maier, Schliengen; Helmut Luther, Grenzach-Wyhlen, both of Germany

[73] Assignee: Ciba Specialty Chemicals Corporation, Tarrytown, N.Y.

[21] Appl. No.: 624,379

[22] PCT Filed: Sep. 24, 1994

[86] PCT No.: PCT/EP94/03187

§ 371 Date: Apr. 3, 1996

§ 102(e) Date: Apr. 3, 1996

[87] PCT Pub. No.: WO95/09862

PCT Pub. Date: Apr. 13, 1995

[30] Foreign Application Priority Data

Oct. 6, 1993 [GB] United Kingdom ............ 9320610

[51] Int. Cl.[6] ............ A61K 31/70; A61K 31/07; C07H 31/04
[52] U.S. Cl. .......... 514/25; 514/725; 514/844; 514/859; 536/4.1
[58] Field of Search .......... 514/25, 725, 844, 514/859; 536/4.1

[56] References Cited

U.S. PATENT DOCUMENTS

| | | | |
|---|---|---|---|
| 4,457,918 | 7/1984 | Holick et al. | 514/25 |
| 4,565,863 | 1/1986 | Bollag et al. | 536/18.2 |
| 5,045,533 | 9/1991 | Philippe et al. | 514/29 |
| 5,091,522 | 2/1992 | Philippe et al. | 536/17.2 |

FOREIGN PATENT DOCUMENTS

| | | |
|---|---|---|
| 0315540 | 5/1989 | European Pat. Off. |
| 356154 | 2/1990 | European Pat. Off. |
| 0388308 | 9/1990 | European Pat. Off. |
| 2598420 | 5/1986 | France |
| 2191483 | 12/1987 | United Kingdom |
| 90/14093 | 11/1990 | WIPO |
| 93/21195 | 10/1993 | WIPO |

OTHER PUBLICATIONS

Barua, Arum B. *Methods Enzymology*, vol. 189 (Retinoids, Pt. A), pp. 136–145, (1990).

Pfander et al. *Helvetica Chimica Acta*, vol. 63(1), 277–283, (1980).

Pfander, Hanspeter. *Pure & Applied Chem.*, vol. 51, 565–580, (1979).

Ed. by Collins & Ferrier. *Monosaccharides: Their Chemistry and Their Roles in Natural Products* (John Wiley & Sons), p. 4, (1995).

Barua et al., *International J. Vit. Nutr. Res.* 61 258–263 (1991).

*Primary Examiner*—John Kight
*Assistant Examiner*—Howard C. Lee
*Attorney, Agent, or Firm*—Kevin T. Mansfield

[57] ABSTRACT

The invention relates to water-soluble sugar retinoids (I) and to their preparation and the use thereof as medicaments and in the cosmetic sector, wherein X is a sugar radical attached at an oxygen atom, i.e. a mono-, di- or oligosaccharide, provided that X is not a glucose or galactose sugar residue attached at the oxygen atom in the respective 1-positions of the glucose or galactose residues.

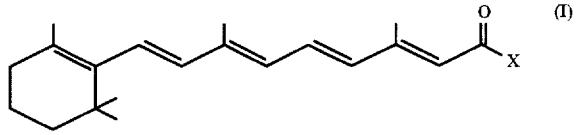

12 Claims, No Drawings

WATER-SOLUBLE RETINOIDS

The present invention relates to water-soluble novel sugar retinoids, and to their preparation and the use thereof as medicaments and in the cosmetic sector.

Retinoic acid derivatives are commonly used in the field of dermatology. Thus keratinising epithelial tissue can be converted by retinoic acid or derivatives thereof into tissue of normally differentiated cells. The retinoids exert a protective action against chemically, photochemically or virally induced carcinogenesis and assume protective functions in cell division. Retinoic acid itself is water-insoluble and is therefore usually converted into a water-soluble form for ease of handling.

Aromatic retinoids having a saccharide or aminosaccharide radical, and which are suitable dermatalogical agents for use in pharmaceuticals and cosmetics, are disclosed in U.S. Pat. No. 4,565,863. For toxicological reasons, such aromatic retinoids are sought to be avoided.

Certain new water-soluble aliphatic derivatives of retinoic acid have now been found which are excellent dermatalogical agents for use in pharmaceuticals and cosmetics.

Accordingly, the present invention provides retinoic acid esters of formula (I)

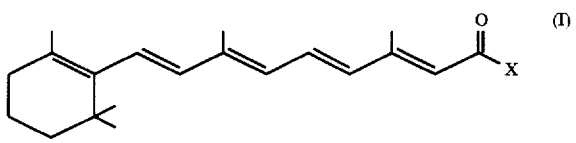

wherein X is a sugar residue attached at an oxygen atom, i.e. a mono-, di- or oligosaccharide, provided that X is not a glucose- or galactose sugar residue attached at the oxygen atom in the respective 1-positions of the glucose- or galactose sugar residues.

The double bonds in the retinoic acid radical may be in cis- or trans-configuration, the all-trans-form being preferred.

Oligosaccharides containing more than two sugar units may suitably be in particular compounds such as streptomycin, neuraminic acid, fucose, $\alpha,\beta,\gamma$-cyclodextrin, raffinose or short-chain degradation products of amylose or cellulose.

The sugar radical is preferably a mono- or disaccharide which is derived from ribose, arabinose, xylose, glucose, mannose, galactose, lactose, saccharose, trehalose, cellobiose, maltose, fructose or derivatives thereof.

Suitable derivatives of these sugars include: desoxy sugars; the lactones of the corresponding sugar acids such as gluconic acid γ-lactone which in turn may be esterified by $C_1$–$C_4$alkyl; uronic acids; amino sugars having an unsubstituted amino group, typically glucosamine, fructosamine, galactosamine, or having a $C_1$–$C_6$alkyl- or $C_1$–$C_6$acetyl-substituted amino group, e.g. aminoethylglucosides, aminoethyl-2-deoxy-2-aminoglucoside, N-acetylaminoglucoside; sugars in which the OH groups are substituted by one or more than one $C_1$–$C_4$alkoxy group, e.g. methyl or ethyl glucose, substitution by $C_1$–$C_4$alkylene bridges also being possible; keto-sugar acids such as ascorbic acid; sugars in which the OH groups are mono- or polyacetylated, typically glucose acetate or 2,3,4-tri-O-acetylglucose; or sugars carrying several different substituents, e.g. neuraminic acid.

Particularly preferred sugars are glucose, galactose, mannose or derivatives thereof.

The aforementioned sugar radicals may also be in the form of racemates or any mixtures of the (L)- and (D)-configuration as well as in the form of the pure (L)- or (D)-isomers. The natural (D)-configuration is preferred.

Compounds of formula Ia, Ib or Ic are of particular importance:

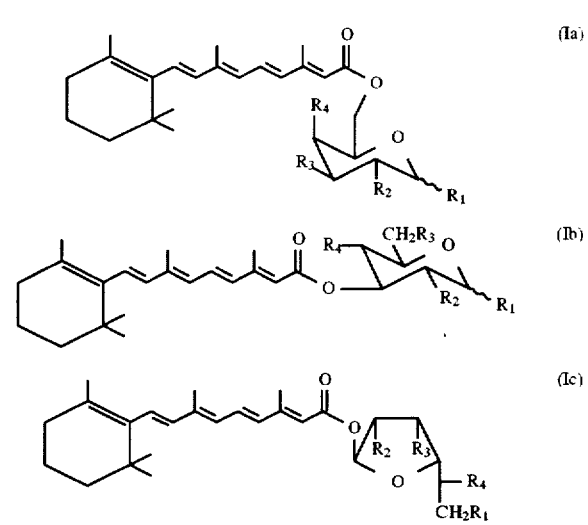

wherein
$R_1$, $R_2$, $R_3$ and $R_4$ are OH, $C_1$–$C_4$alkoxy, $C_1$–$C_3$alkylCOO—, or two of these radicals taken together are a O—$C_1$–$C_4$—O-alkylene bridge;

as well as the isomers of the compounds (Ia) and (Ib) in which the saccharide moiety is in the furanose form.

The novel compounds of formula (I) are prepared by
a) converting retinoic acid into a reactive derivative, and
b) adding a mono-, di- or oligosaccharide.

To enhance its reactivity, the retinoic acid can be converted into a reactive derivative such as an imidazolide, a mixed anhydride or an acid chloride. The acid chloride is preferred. This conversion is preferably carried out with chloroenamine or dimethylchloroformamidinium chloride, using any solvent which is inert to the chlorinating reagent and which at least partially dissolves the retinoic acid, conveniently selected from among ethers, amides, aromatic hydrochlorides, esters, halogenated hydrocarbons, nitrites and sulfoxides. Typical examples of such solvents are methylene chloride, dimethyl formamide, toluene, ethyl acetate, acetonitrile, dimethyl sulfoxide and hexane.

To obtain the retinoic acid esters of formula I, Ia, Ib or Ic, the sugar can be used in already derivatised form or it is derivatised after the linkage to the retinoic acid or after the sulfation. It is preferred to use sugars in which the OH groups that are not to be esterified are provided with protective groups so as to achieve a selective linkage of the sugar to the acid chloride. The protective groups used for this purpose are normally diol protective groups such as isopropylidene, benzylidene or ethylene protective groups, and they are prepared in known manner. After the linkage of the sugar to the retinoic acid, these groups can be removed again in known manner.

The reaction of the sugar with the retinoic acid derivative preferably takes place under the same conditions as are used for the derivatisation of the retinoic acid, and a base such as pyridine can be added to promote the reaction.

It has been found that the compounds of formula (I) can be used for the cosmetic and pharmacological treatment of the eyes or skin, for example for tautening and rejuvenating the skin, for the treatment of acne, psoriasis, neoplasms, dermatoses, as well as for preventive treatment to provide protection from ultraviolet radiation.

For pharmaceutical application, the compounds of formula (I) are formulated with conventional carriers.

Topical application is preferred. Such application comprises treating the skin with an effective amount of the compound of formula (I).

A pharmaceutical or cosmetic composition containing a compound of formula (I) may be administered or applied in the form of tablets, granules, capsules, dragées, ointments, creams, tinctures, lotions, solutions, suspensions, hydrogels, liposomes or foam sprays.

Suitable carriers include mixtures of different emulsifiers, dispersants, stabilisers, perfume oils, antioxidants, thickeners, diluents, humectants, fillers, salts for changing the osmotic pressure, and buffers. Typical examples of such carriers are gelatin, lactose, starch, fatty acid salts, talcum, gum arabic, polyalkylene glycols and other non-toxic excipients.

The concentration of active ingredient may be from 0.01 to 5 % by weight, depending on the dosage form.

The following examples illustrate the invention.

EXAMPLE 1
Linkage of retinoic acid to 1,2:3,4-diisopropylidene-α-D-galactopyranose

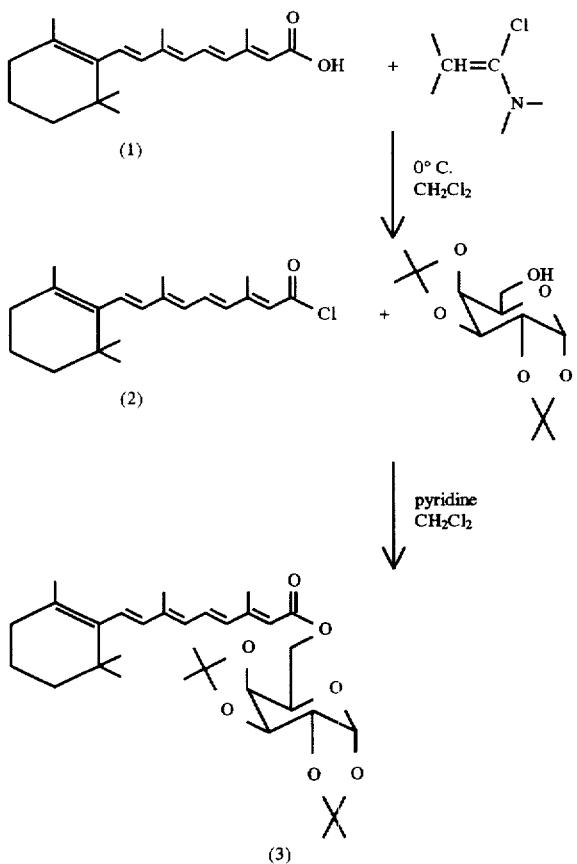

21 g of all-trans-retinoic acid (1) are suspended, under nitrogen, in 250 ml of methylene chloride. With stirring, 9.9 ml of chloroenamine are slowly added to the suspension. The clear orange solution is stirred for a further 30 minutes at 0° C. To this solution is added a solution of 1,2:3,4-diisopropylidene-α-D-galactopyranose in 70 ml of methylene chloride and 11 ml of pyridine. After this addition, the ice bath is removed and stirring is continued for another hour. For working up, the solution is concentrated to dryness and the residue is taken up in petroleum/ethyl acetate (15/1) and purified over a silica gel column with petroleum ether/ethyl acetate (15/1). The yield of all-trans-1,2:3,4-diisopropylidene-6-retinoyl-α-D-galactopyranose (3) is from 73 to 87%.

Removal of the protective groups 25 g of 1,2:3,4-diisopropylidene-6-retinoyl-(α-D-galactopyranose (3) are dissolved in 200 ml of tetrahydrofuran. Then 20 ml of 2N sulfuric acid are added and the reaction mixture is refluxed for 12 hours. For working up, the reaction solution is neutralised with sodium hydrogencarbonate, and the product is extracted with methylene chloride, concentrated to dryness on a rotary evaporator and taken up in methylene chloride/methanol (7/1) and purified over a silica gel column with methylene chloride/methanol (7/1).

The yield of product of formula (4) is 79%.

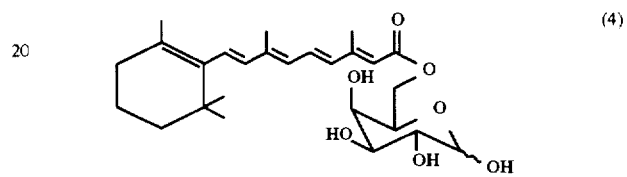

The protected α-D-galactopyranose of Example 1 is replaced with the following sugars (unprotected or in suitably protected form): ribose, arabinose, xylose, lactose, saccharose, trehalose, cellobiose, maltose, fructose, neuraminic acid, fucose, α,β,γ-cyclodextrin or raffinose, to give water-soluble derivatives of retinoic acid which can be used for the cosmetic and pharmacological treatment of the eyes or skin.

EXAMPLE 2

In accordance with the general procedure described in Example 1, reaction of all-trans-retinoic acid (1) and 1,2:5,6-di-O-isopropylidene-D-glucose, followed by subsequent removal of the protective groups, gives a compound of formula (5)

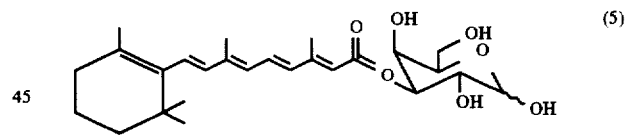

EXAMPLE 3

In accordance with the general procedure described in Example 1, reaction of all-trans-retinoic acid (1) and 1,2:4,5-di-O-isopropylidene-D-fructose, followed by subsequent removal of the protective groups, gives a compound of formula (6)

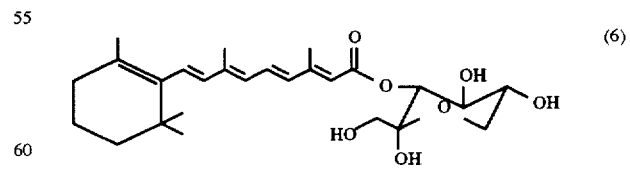

EXAMPLE 4

In accordance with the general procedure described in Example 1, reaction of all-trans-retinoic acid (1) and 2,3:5,6-di-O-isopropylidene-α-D-mannofuranose; followed by subsequent removal of the protective groups, gives a compound of formula (7)

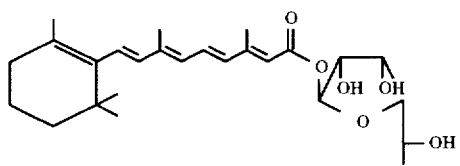

EXAMPLE 5

A cream of the following composition is prepared 0.05% of the compound of formula (5) of Example 2
2.00% of Amphisol®
2.50% of stearic acid
3.50% of glyceryl myristate
5.00% of isopropyl myristate
3.00% of 1,2-propylene glycol
0.10% of triethanolamine
0.55% of sodium hyalurate
0.02% of propyl parabene
0.18% of methyl parabene
perfume oils as required, and demineralised water to make up 100%

The triethanolamine, sodium hyalurate, parabene, propylene glycol and water are heated to 75° C. and a mixture of the fat-soluble components, also heated to 75° C., is added, and the entire mixture is homogenised. After cooling, with stirring, to 40° C., the monosaccharide retinoic acid ester (5) and optional perfume oils are added.

EXAMPLE 6

The procedure of Example 5 is repeated, but using a compound of formula (4) of Example 1 as monosaccharide.

EXAMPLE 7

The procedure of Example 5 is repeated, but using a compound of formula (6) of Example 3 as monosaccharide.

EXAMPLE 8

The procedure of Example 5 is repeated, but using a compound of formula (7) of Example 4 as monosaccharide.

EXAMPLE 9

A transparent hydrogel of the following composition is prepared:

0.1% of the compound of formula (5) Example 2
20.0% of 1,2-propylene glycol
20.0% of isopropanol
2.0% of acrylic acid polymer
3.0% of triethanolamine
perfume oils as required, and demineralised water to make up 100%

The acrylic acid polymer and water are dispersed and the dispersion is neutralised with triethanolamine. The monosaccharide retinoic acid ester (5) is dissolved in a mixture of isopropanol and propylene glycol and the solution is mixed with other components to a gel.

EXAMPLE 10

The procedure of Example 9 is repeated, but using a compound of formula (4) of Example 1 as monosaccharide.

EXAMPLE 11

The procedure of Example 9 is repeated, but using a compound of formula (6) of Example 3 as monosaccharide.

EXAMPLE 12

The procedure of Example 9 is repeated, but using a compound of formula (7) of Example 4 as monosaccharide.

EXAMPLE 13

A foam spray of the following composition is prepared:

0.03% of the compound of formula (5) of Example 2
5.00% of 1,2-propylene glycol
1.70% of cetyl alcohol
1.00% of paraffin oil, viscous
2.00% of isopropyl myristate
2.40% of Cetomacrogol 1000®
1.50% of sorbitan monostearate
0.18% methyl parabene
0.10% propyl parabene
0.10% of Chemoderm 314®
perfume oils as required, and demineralised water to make up 100%

Cetyl alcohol, paraffin oil, isopropyl myristate, Cetomacrogol 1000® and sorbitan stearate are fused and the methyl- and propyl parabene, dissolved in propylene glycol, and hot water are added at 75° C. and the mixture is homogenised. After cooling to 40° C., the monosaccharide retinoic acid ester (5), Chemoderm 314® and optional perfume oils are added. 20 ml of the mixture are filled into an aluminium lacquer-coated container which is closed with a valve and filled with propellant gas under pressure.

EXAMPLE 14

The procedure of Example 13 is repeated, but using a compound of formula (4) of Example 1 as monosaccharide.

EXAMPLE 15

The procedure of Example 13 is repeated, but using a compound of formula (6) of Example 3 as monosaccharide.

EXAMPLE 16

The procedure of Example 13 is repeated, but using a compound of formula (7) of Example 4 as monosaccharide.

EXAMPLE 17

In accordance with the test method of L. H. & A. M. Kligman [The effect on rhino mouse skin of agents which influence keratinisation and exfoliation, J.Invest.Dermatol., 73, 354–358 (1979)], rhino mice are treated for 3 weeks, twice a day, each time with a) a 0.05% solution of the compound of formula (5), namely glucose retinate, or with b) a 0.025% solution of retinic acid, the solvent in each case being ethanol:polyethylene glycol (90:10, v:v).

The two test compounds provide a comparable normalisation of the skin structure (reduction of the utriculi). Retinic acid, however, causes, as a side effect, a significant reddening of the skin, which undesirable effect is not observed with the compound of formula (5).

EXAMPLE 18

In order to detect any possible teratogenic effect, the compound of formula (5) is tested, using retinic acid as a comparison, in a rat embryo culture using the method of L. Cicurel & B. P. Schmid [Postimplantadon embryo culture for the assessment of the teratogenic potential and potency of compounds, Experientia 44, 833–40 (1988)]. Whereas retinic acid induces malformations, even at a concentration of 0.3 μg/ml, no malformations occur at up to 10 μg/ml with the compound of formula (5).

What is claimed is:

1. A compound of formula Ia, Ib or Ic

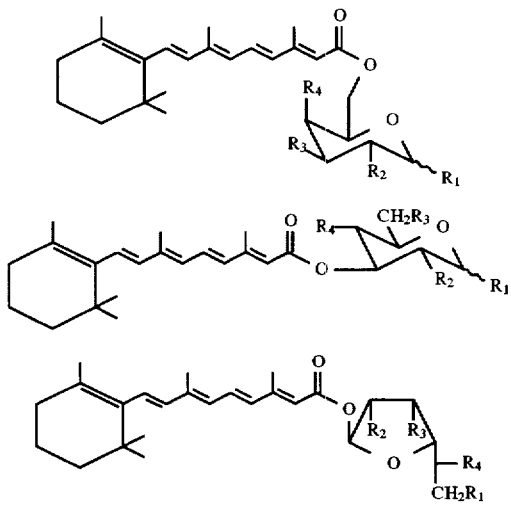

wherein $R_1$, $R_2$, $R_3$ and $R_4$ are OH, $C_1$–$C_4$alkoxy, $C_1$–$C_3$alkylCOO—, or two of these radicals taken together are a O—$C_1$-$C_4$—O-alkylene bridge;

or an isomer of the compounds (Ia) and (Ib) in which the saccharide moiety is in the furanose form.

2. A compound according to claim 1, wherein each of the substituents $R_1$, $R_2$, $R_3$ and $R_4$ is OH.

3. A process for the preparation of a compound of the formula Ia, Ib or Ic as claimed in claim 1, which comprises a) converting retinoic acid into a reactive derivative and b) adding an appropriate mono-, di- or oligosaccharide.

4. A process for the preparation of a compound of formula Ia, Ib, or Ic according to claim 2, which comprises converting retinoic acid into an acid chloride.

5. A process for the preparation of a compound of formula Ia, Ib, or Ic according to claim 4, which comprises converting retinoic acid into an acid chloride with chloroenamine or dimethylchloroformamidinium chloride.

6. A process for the preparation of a compound of formula Ia, Ib, or Ic according to claim 5, which comprises carrying out the reaction with chloroenamine.

7. A process for the preparation of a compound of the formula Ia, Ib or Ic according to claim 3, wherein the mono-, di- or oligosaccharide carries protective groups.

8. A process for the preparation of a compound of formula Ia, Ib, or Ic according to claim 7, which comprises using diol protective groups as protective groups for the saccharide.

9. A process for the preparation of a compound of formula Ia, Ib, or Ic according to claim 7, which comprises removing the protective groups for the saccharide again after the linkage of the sugar to the retinoid.

10. A pharmaceutical or cosmetic composition comprising a pharmaceutically or cosmetically effective amount of a compound as claimed in claim 1 and a pharmaceutically or cosmetically acceptable carrier.

11. A method for the treatment of acne, psoriasis, skin neoplasms, dermatoses and for preventive treatment to provide protection from ultraviolet radiation, which comprises administering to a host in need of said treatment a composition as claimed in claim 10.

12. A method according to claim 11 which consists of topical application of the composition.

* * * * *